(12) United States Patent
Lederman et al.

(10) Patent No.: US 8,513,603 B1
(45) Date of Patent: *Aug. 20, 2013

(54) IN-SITU DETERMINATION OF THIN FILM AND MULTILAYER STRUCTURE AND CHEMICAL COMPOSITION USING X-RAY FLUORESCENCE INDUCED BY GRAZING INCIDENCE ELECTRON BEAMS DURING THIN FILM GROWTH

(75) Inventors: David Lederman, Morgantown, WV (US); Thomas Hubbard Myers, II, New Braunfels, TX (US); Sandeep Chandril, Dehradun (IN)

(73) Assignee: West Virginia University, Morgantown, WV (US)

( * ) Notice: Subject to any disclaimer, the term of this patent is extended or adjusted under 35 U.S.C. 154(b) by 347 days.

This patent is subject to a terminal disclaimer.

(21) Appl. No.: 13/068,483

(22) Filed: May 12, 2011

Related U.S. Application Data

(60) Provisional application No. 61/395,340, filed on May 12, 2010.

(51) Int. Cl.
*G21K 7/00* (2006.01)
*H01J 37/26* (2006.01)

(52) U.S. Cl.
USPC ........... 250/310; 250/305; 250/306; 250/307; 250/492.3; 700/90; 700/109; 700/110; 702/27; 702/28; 702/127; 702/134; 378/6; 378/44; 378/45

(58) Field of Classification Search
USPC ................. 250/305, 306, 307, 309, 310, 311, 250/492.1, 492.3; 702/27, 28, 127, 134; 700/90, 109, 110; 378/5, 44, 45
See application file for complete search history.

(56) References Cited

U.S. PATENT DOCUMENTS

| 5,798,525 A * | 8/1998 | Benizri-Carl et al. ........ 250/310 |
| 2010/0017172 A1* | 1/2010 | Statham et al. .................. 703/2 |

* cited by examiner

*Primary Examiner* — Robert Kim
*Assistant Examiner* — Nicole Ippolito
(74) *Attorney, Agent, or Firm* — William Aylor

(57) ABSTRACT

A method utilizing characteristic x-ray emission from a single thin film or multilayer thin film when an electron beam impinges at a grazing angle with respect to the surface of the sample to capture structural and physical properties of the layers such as layer thickness, interfacial roughness, and stoichiometry of the sample.

16 Claims, 15 Drawing Sheets

IN-SITU DETERMINATION OF THIN FILM AND MULTILAYER STRUCTURE AND CHEMICAL COMPOSITION USING X-RAY FLUORESCENCE INDUCED BY GRAZING INCIDENCE ELECTRON BEAMS DURING THIN FILM GROWTH

CROSS-REFERENCE TO RELATED APPLICATIONS

This application claims priority from U.S. provisional application numbered 61/395,340 filed on May 12, 2010.

STATEMENT REGARDING FEDERALLY SPONSORED RESEARCH OR DEVELOPMENT

This invention was made with government support under Grant No. F49620-03-1-0330 awarded by the US Air Force Office of Scientific Research and Grant No. N00014-02-1-0974 awarded by the US Office of Naval Research. The United States government has certain rights in the invention.

REFERENCE TO SEQUENCE LISTING, A TABLE, OR A COMPUTER PROGRAM LISTING COMPACT DISC APPENDIX

BRIEF DESCRIPTION OF THE SEVERAL VIEWS OF THE DRAWINGS

The following figures are not drawn to scale and are for illustrative purposes only.

DETAILED DESCRIPTION OF THE INVENTION

Figure 1:
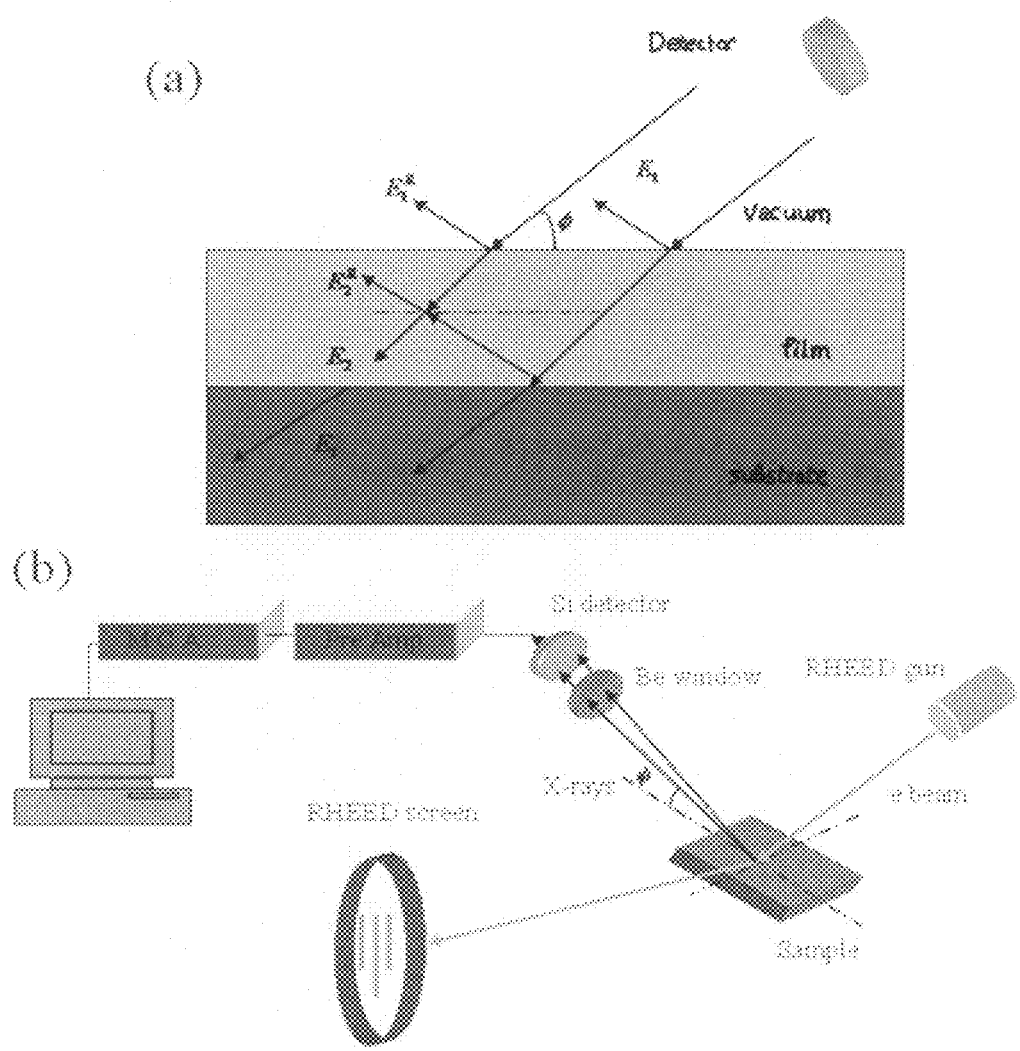
FIG. 1 (a) is an illustration of the reciprocity theorem used to calculate the electric field amplitude inside a thin layer over a substrate. Reflectivity at any interface can be calculated using Parratt's approach in case of a multilayered structure while (b) is a schematic illustration of the set-up used for RHEED-TRAXS experiments.

Reflection high energy electron diffraction (RHEED) is a commonly used surface analysis technique implemented during molecular beam epitaxy (MBE), pulsed laser deposition (PLD), and other techniques used in the growth of thin film materials.[1] Aside from the utility of the electron diffraction produced, RHEED electrons impinging upon the sample surface also produce x-ray fluorescence that can be used to probe a thin film's elemental composition. In-situ surface and compositional analysis using x-rays generated by RHEED has been previously reported and is generally referred to as RHEED-total-reflection-angle x-ray spectroscopy (RHEED-TRAXS). RHEED-TRAXS measurements are performed at take-off angles close to the angle of total external reflection of the emitted x-rays, thus enhancing surface sensitivity. In particular, Hasegawa et al. have studied the adsorption and desorption processes of silver on silicon and Braun et al. have carried out real-time analysis showing sub-monolayer sensitivity and surface roughness effects, but the methods described in those papers are primarily qualitative in nature. [2][3]

A first embodiment can be a method utilizing characteristic x-ray emission from a single thin film or multilayer thin film when an electron beam impinges at a grazing angle with respect to the surface of the sample to capture structural and physical properties of the layers such as layer thickness, interfacial roughness, and stoichiometry of a compound layer. In this method x-rays are detected at a grazing angle with respect to the surface of the sample. This data analysis is based on principles similar to the analysis of a multilayered structure by angular-dependent total reflection of x-rays (AD-TRX), a technique where x-rays (not electrons) are incident on the sample at grazing angles and x-ray fluorescence is detected [1] W. Braun, Applied RHEED (Springer, Berlin, 1999). [2] S. Hasegawa, H. Daimon, and S. Ino, Surface Science 186, 138 (1987). [3] W. Braun and K. H. Ploog, Journal of Crystal Growth 251, 68 (2003). [4]. The angular dependence of the energy dispersive spectrum of the x-ray fluorescence radiation can yield structural and chemical information about the layered structure because the critical angle and the shape of the angular dependence are dependent upon the film's thickness and on properties of overlying and underlying layers. This measurement permits determination of structural information, including film thickness and interface roughness. Accurate structural determination requires analyzing the penetration of the electron beam in the sample as described below.

Stoichiometry (chemical composition) of a compound layer or multilayer can also be determined. This is possible because the angular distribution of the x-ray emission for every element is dependent upon its fractional composition and refractive index of the film matrix. Accurate stoichiometry determination requires measuring at take-off angles greater than the critical angle for each element's characteristic emission, as described below in [0068].

According to the reciprocity theorem, the intensity of x-rays emitted from a depth z inside a medium and observed at a grazing exit angle is proportional to the x-ray intensity which is impinging at the same grazing incident angle and observed at the depth z inside the medium [5], [6]. Therefore, within the distorted-wave approximation, the intensity of x-rays generated from homogeneous scattering centers (e.g., atoms) inside the film and reaching the detector are proportional to the plane waves coming off the detector position, distorted by the dielectric constant of the layer material and diffracted off the scatterers with no further interaction with the medium (FIG. 1(a)) [7]. Hence, the fluorescence intensity at grazing exit can be evaluated using the same approach as the electric field intensity under grazing incidence conditions.

For a grazing incidence angle $\phi$, the total electric field amplitude at distance z from the film's surface in the nth layer can be written as $$E_n^{Total}(z,\phi) = E_n e^{\left(-i\frac{2\pi z f_n}{\lambda}\right)} + E_n^R e^{\left(-i\frac{2\pi z f_n}{\lambda}\right)}, \quad (1)$$

where $\lambda$ is the wavelength of the detected x-rays, $E_n$ is the amplitude of the transmitted wave into the nth layer and $E_n^R = R_{n,n+1} E_n$ is the amplitude of the wave reflected from the interface between the nth and (n+1)th layers. The refracted angle in the nth layer is $$f_n = (\phi^2 - 2\delta_n - 2i\beta_n)^{1/2}, \quad (2)$$

where $\delta$ and $\beta$ are associated with the dispersion and absorption in the medium, respectively. The reflectance $R_{n,n+1}$ can be calculated using Parratt's recursive approach [8]. If $R_{n,n+1} = E_n^R/E_n$, then $$R_{n-1,n} = a_{n-1}^2 \cdot \left[\frac{R_{n,n+1} + F_{n-1,n}}{R_{n,n+1} \cdot F_{n-1,n} + 1}\right], \quad (3)$$

where $$F_{n-1,n} = \frac{f_{n-1} - f_n}{f_{n-1} + f_n}, \quad (4)$$

and $$a_n = \exp(-i2\pi f_n d_n/\lambda). \quad (5)$$

Thus, the reflectance from all interfaces can be determined starting from the bottom layer. Interfacial roughness was treated by the introduction of a roughness factor $Q_n$ such that $F_{n,n+1}^{Rough} = Q_n F_{m,n+1}$, where $Q_n = \exp(2\sigma_n^2 k_n k_{n+1})$ is the Nevot-Croce factor and $\sigma_n$ is the root-mean-squared value of the vertical roughness [9]. The x-ray propagation wave vectors in the nth and (n+1)th layers are $k_n$ and $k_{n+1}$, respectively.

The total intensity at a grazing angle $\phi$ was obtained by integrating the intensity from each point in the film such that the total intensity from a film thickness of $d_n$ is $$I(\phi) \propto \int_0^{d_n} I_{x-ray}(z)|E_n^{Total}(z,\phi)|^2 dz. \quad (6)$$

$I_{x-ray}(Z)$ is the x-ray depth profile and is necessary to scale the intensity term $|E_n^{Total}|^2$ because x-rays are generated by inelastic scattering of electrons grazing the surface and have strong depth dependence.

The x-ray depth profile can be generated by simulating the electron trajectories inside the film(s). This can be done using specialized software such as CASINO (monte CArlo Simulation of electroN trajectories in sOlids), a free, versatile software, although any other software using a Monte Carlo or other approaches for calculating electron trajectories may be used. This was used to model $I_{x-ray}(z)$ based on energy losses in inelastic scatterings in the limit of the continuous slow down approximation [10].

Equation (6) depends on the thickness of the probed layer explicitly and through the term $|E_n^{Total}|^2$, which contains the structural information of the overlayers and underlayers as well. Thus, it can be used to estimate structural parameters of a multilayered structure by parameter fitting method if fluorescence intensity is recorded as a function of take-off angle, $\phi$.

Further, equation (6) is valid for an ideally parallel beam. The beam divergence due to a collimating slit can be accounted for by convoluting the intensity distribution with a Gaussian function $G(\phi-\theta)$ centered at the slit. Hence, the final simulated intensity at angle $\phi$ is $$I^{Total}(\phi) \propto \frac{\int_{-\infty}^{\infty} I(\phi) G(\phi-\theta) d\theta}{\int_{-\infty}^{\infty} G(\phi-\theta) d\theta} \quad (7)$$

The depth profile $I_{x\text{-}ray}(z)$ is independent of the thickness of the film as the secondary fluorescence in the film due to the x-ray coming off the substrate or other layers is ignored. For layers buried under material(s), the thickness of the overlayer(s) affects the number of electrons with sufficient energy for ionization reaching the layer and thus the depth profile. So for buried layers, $I_{x\text{-}ray}(z)$ to be used in Eq. (7) is initially calculated using a sufficiently thick overlayer(s) and then using the thickness values obtained from Eq. (7) by parameter fitting method for successive Monte Carlo simulations, until convergence is reached. Each simulation was carried out with at least 100,000 electrons in order to produce statistically significant profiles.

In the experimental set-up, an electron gun is aimed at grazing angle incidence (smaller than 5° with respect to the sample's surface). The energy of the electrons must be at least as large as the minimum characteristic x-ray fluorescence energy of interest. The power supply controller of the electron gun must be sufficiently stable to control the emission current to within 1%. This can be done with a feedback circuit.

An x-ray detector is placed to capture the emitted x-ray fluorescence at a grazing angle with respect to the sample's surface. The detector may be placed anywhere in the plane of the surface of the sample. The opening of the detector must be sufficiently small to allow for discrimination of take-off angles (the angle of the detector with respect to the sample surface). The x-ray detector must be on a moveable arm to allow capturing of data as a function of take-off angle. The x-ray detector must be able to discriminate incoming fluorescence with respect to its energy.

The sample must be in a vacuum environment sufficiently clean to prevent surface contamination and x-ray absorption.

Data at the characteristic x-rays of interest are acquired as a function of take-off angle by moving the detector to different take-off angle positions.

The absolute take-off angle can be determined by scanning the substrate material or a thick reference sample (greater than 1 μm). Using the model above for a single layer of large thickness, the absolute take-off angle can be calculated and the measurements of the actual film sample determined as long as the actual sample is at the same position as the calibration reference sample.

The intensity data are then modeled using the method described above to obtain layer thickness and roughness parameters.

The stoichiometry can be determined as follows. The intensity as a function of take-off angle will in general rise quickly as a critical angle is reached. This critical angle depends on the index of refraction of the material, which in turn depends on the wavelength of the fluorescence radiation. Therefore, different x-ray energies will have different critical angles. As the angle is increased further, the will intensity level off. At angles much greater than the critical angle, the intensity at the elemental characteristic x-ray emission energies is recorded. A similar measurement made on a known sample may be used as a calibrated reference by carrying the same measurement under similar conditions. This reference measurement determines the relative sensitivity of the apparatus to the different elemental x-ray energies. Characteristic x-rays can include $K_\alpha$, $K_\beta$, $L_\alpha$, $L_\beta$, or any other inner-core emission characteristic of each element present in the sample of interest. The only requirement is that the energy of the incoming electron beam be larger than the emission energy of interest.

For example, if the reference sample is composed of elements A1 and A2 and a measurement of the reference yields intensities I1 and I2, and it is known that the atomic concentrations of A1 and A2 are x and 1−x, respectively, the relative sensitivity factors to element A1 and A2 become S1/S2=x/(1−x).

The intensity may be the number of counts at the peak energy or the integral of the number of counts under the energy peak.

Information about the chemical composition of the thin film can be used in a feedback loop to control during the deposition process of the thin film to obtain a thin film with a desired chemical composition. In order to do this, the ratio of the intensity of the characteristic x-rays corresponding to the elements of interest are monitored during thin film deposition process. If the intensity of one of the elements' x-rays is larger than desired, the evaporation rate of that source is decreased. The evaporation source can be a thermal evaporation cell, a sputtering gun, or any other deposition technique that permits acquisition of the characteristic x-ray fluorescence.

If the time window over which x-ray intensity is acquired is $\Delta t$, the total number of x-ray counts at the peak of interest is $N = R \Delta t$, where R is the rate of x-ray Counts at the detector in counts per second. Because the uncertainty in the number of counts is well known to be $\sqrt{N}$, the fractional uncertainty in the stoichiometry determination during growth is $$\sigma_x/x = \sqrt{N}/N = 1/\sqrt{R \Delta t}. \quad (8)$$

Therefore, the uncertainty can be reduced to a desirable level by increasing the rate or increasing the measurement time. The rate can be increased by increasing the electron gun emission current.

EXAMPLES

The following examples are for illustrated purposes only and not intended to limit the scope of invention.

The experiments were performed in a molecular beam epitaxy (MBE) chamber, with a base pressure of less than $1 \times 10^{-9}$ Torr, dedicated to the growth of oxide materials. The chamber was equipped with a 30 keV RHEED gun (Staib Instruments Inc.) with a custom-built current feedback control capable of producing emission current with a hundredth of a microampere stability for typical operating currents of 1 to 5 microamperes.

The x-ray detector for RHEED-TRAXS was placed on a differentially pumped arm that maintained a base pressure of $1 \times 10^{-7}$ Torr. The arm sat on a 70 mm con-flat port directly in line with the sample position, 690 mm away from the sample and was oriented at 90° to both the RHEED gun and the fluorescent screen. Also, the arm had bellows for vertical movement that allowed the maximum variation of approximately 2° in the detector angle, with respect to the sample surface. X-rays were collimated using a tungsten disk with 1 mm diameter circular aperture giving an angular divergence of 0.7 mrad. The detector assembly had a 25 mm² wide, 500 μm thick Si PIN diode (XR-100CR, Amptek Inc.) and a built-in pre-amplifier. The multichannel analyzer used to collect energy dispersive spectra was the pulse processing assembly PX4 from Amptek Inc. The experimental setup is illustrated in FIG. 1(b).

All the samples were grown on 4 to 6 μm thick hydride vapor phase epitaxy (HVPE) GaN templates on $Al_2O_3$ (0001) single crystal substrates. After being degreased using acetone, trichloroethylene and methanol, they were mounted on an alumina block using indium-tin eutectic.

Single layers of Mn and Y as well as bilayers containing Y on Mn and Mn on Y were deposited on the GaN and capped with Al to prevent oxidation once the sample was removed from the system for ex-situ analysis. Y and Mn were deposited on substrates at room temperature with K-cell temperatures of 1427° C. and 820° C., respectively. The approximate growth rate was 0.09 Å/s for Mn and 0.17 Å/s for Y as measured using a quartz crystal monitor. Al was deposited on top of Y/Mn layer(s) using electron beam deposition with a growth rate of approximately 0.92 Å/s. The films were grown so that they were thick enough to give a statistically significant fluorescence signal and easily analyzable using x-ray reflectivity measurements.

RHEED-TRAXS measurements were done on GaN templates before Y or Mn deposition to accurately calibrate the absolute angle φ using the Ga Kα peak and then after every layer deposition.

The net area of the elemental peaks in the energy dispersive spectrum, obtained by fitting a gaussian peak over the bremsstrahlung background (assumed locally linear for every peak), was used as the measure of the x-ray emission at a given detector angle. The structural parameters, determined from RHEED-TRAXS after every layer deposition, were compared with parameters extracted from the x-ray reflectivity measurements (Tables I-IV).

The Marquardt-Levenberg algorithm was used for parameter estimation from RHEED-TRAXS measurements and the error estimate for ith parameter was calculated as $\sqrt{\sigma_{ii}^2 \chi^2/DOF}$, where $\sigma_{ii}^2$ is the ith diagonal element in the covariance matrix, $\chi^2$ is the goodness of fit, and DOF is the number of degrees of freedom [11]. For the reflectivity measurements, the error estimates are based on monovariate approach and reflect the change in a parameter that doubles the fitness function $F = N^{-1} \|\log x_{meas} - \log x_{fit}\|_2^2$. Here N is the number of data points and $x_{meas}$ and $x_{fit}$ are the measured and calculated counts, respectively.

X-ray reflectivity measurements were carried out using a two-axis goniometer with a Cu rotating anode as a source. A bent-crystal graphite monochromator was used to select the Cu $K_\alpha$ radiation and to focus the beam in the vertical direction at the sample position. Horizontal slits were used to bring the resolution of the instrument to approximately 0.003 Å⁻¹. The off-specular reflectivity was subtracted from the raw data to obtain the true specular reflectivity. Specular reflectivity data were analyzed with the well-known Parratt formalism using the software Parratt32 [12].

Although Y has higher fluorescent yield for Kα radiation than Mn, the combined effect of lower detector efficiency and lower overvoltage ratio i.e., the ratio of the exciting energy to the critical ionization energy, yielded a much smaller signal for Y at 14.96 keV than for Mn at 5.9 keV, with the electron beam of 25 keV energy[13][14]. But, for single layers, the thickness estimates for both Mn and Y layers were in good agreement with the ex-situ estimates. Moreover, the thickness of overlayers could also be estimated using fluorescence from an underlayer. Roughness estimates could only be reported for the investigated layer in most cases as the sensitivity to the over- and underlayers was poor and yielded error estimates that were too large to be analyzed using the Nevot-Croce model (>10 nm)[15]. Also, as the technique is surface sensitive because of the grazing RHEED electrons, the determination of features became less accurate with depth.

Figure 2:
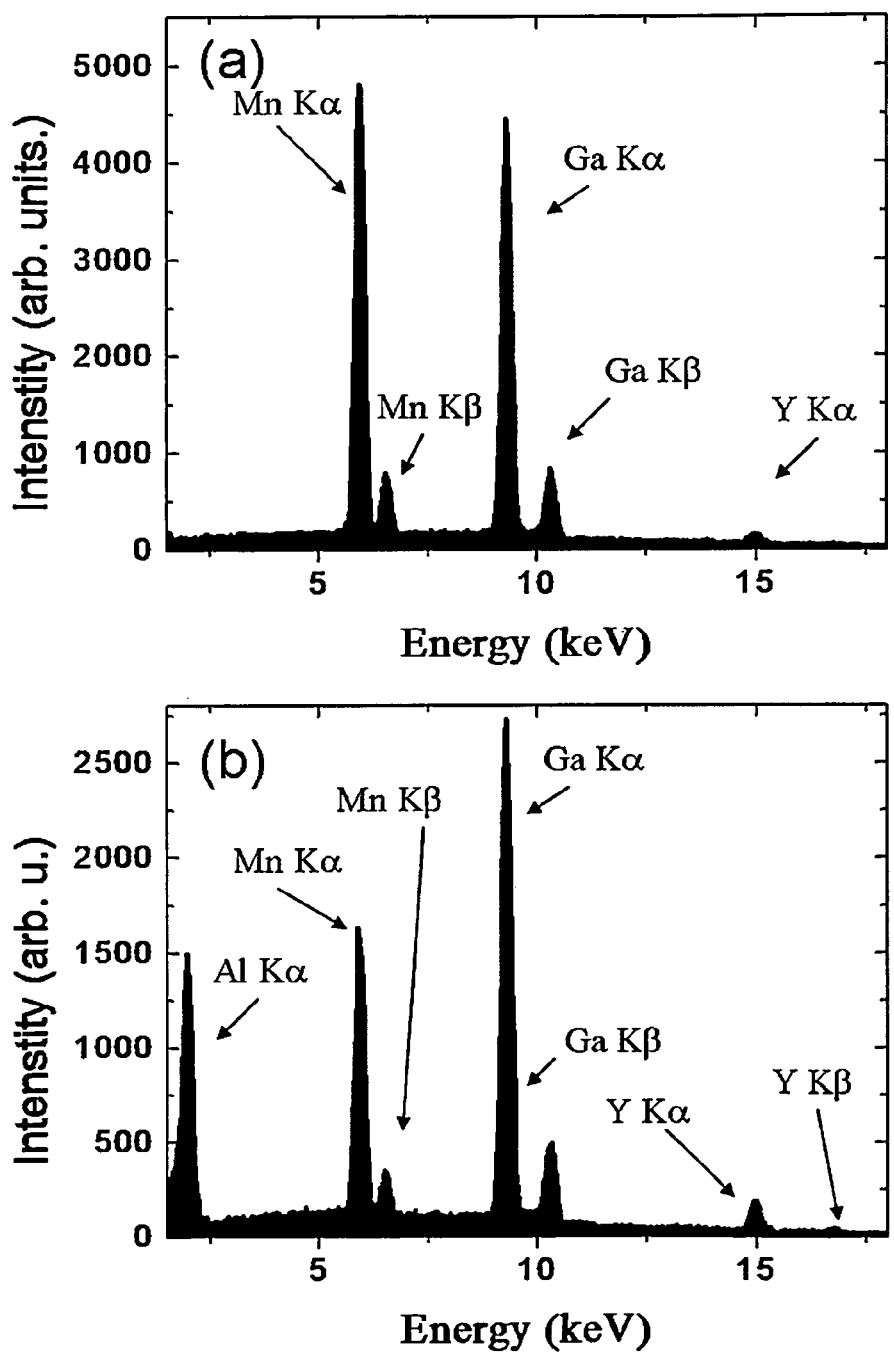
FIG. 2 is the energy dispersive spectrum for Mn on Y(a) and Y on Mn (b) samples at angle of 20 mrad. Clearly visible are the Mn and Ga $K\alpha$, $K\beta$ peaks and Y $K\alpha$ peak. The peak at 1.5 keV in figure (b) is the Al $K\alpha$ peak from the sapphire template.
Figure 3:
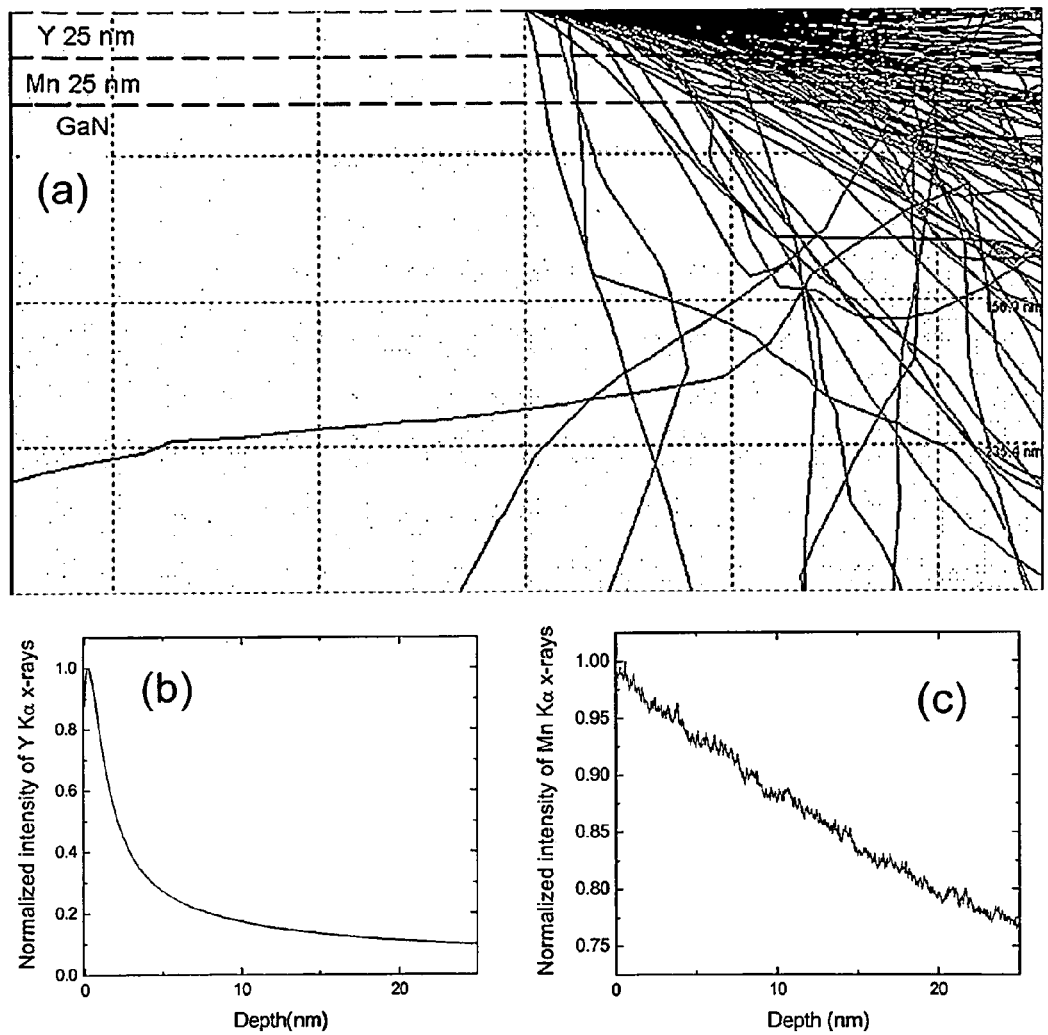
FIG. 3 (a) is the electron trajectories in Y (25 nm) on Mn (25 nm) on GaN sample obtained from CASINO for an electron beam angle of incidence of 2.7° with respect to the sample surface and energy of 25 keV. Only first 200 of 100000 trajectories are displayed. The x-ray depth profile inside (b) Y and (c) Mn layers based on the trajectories in (a) are also shown.
Figure 4:
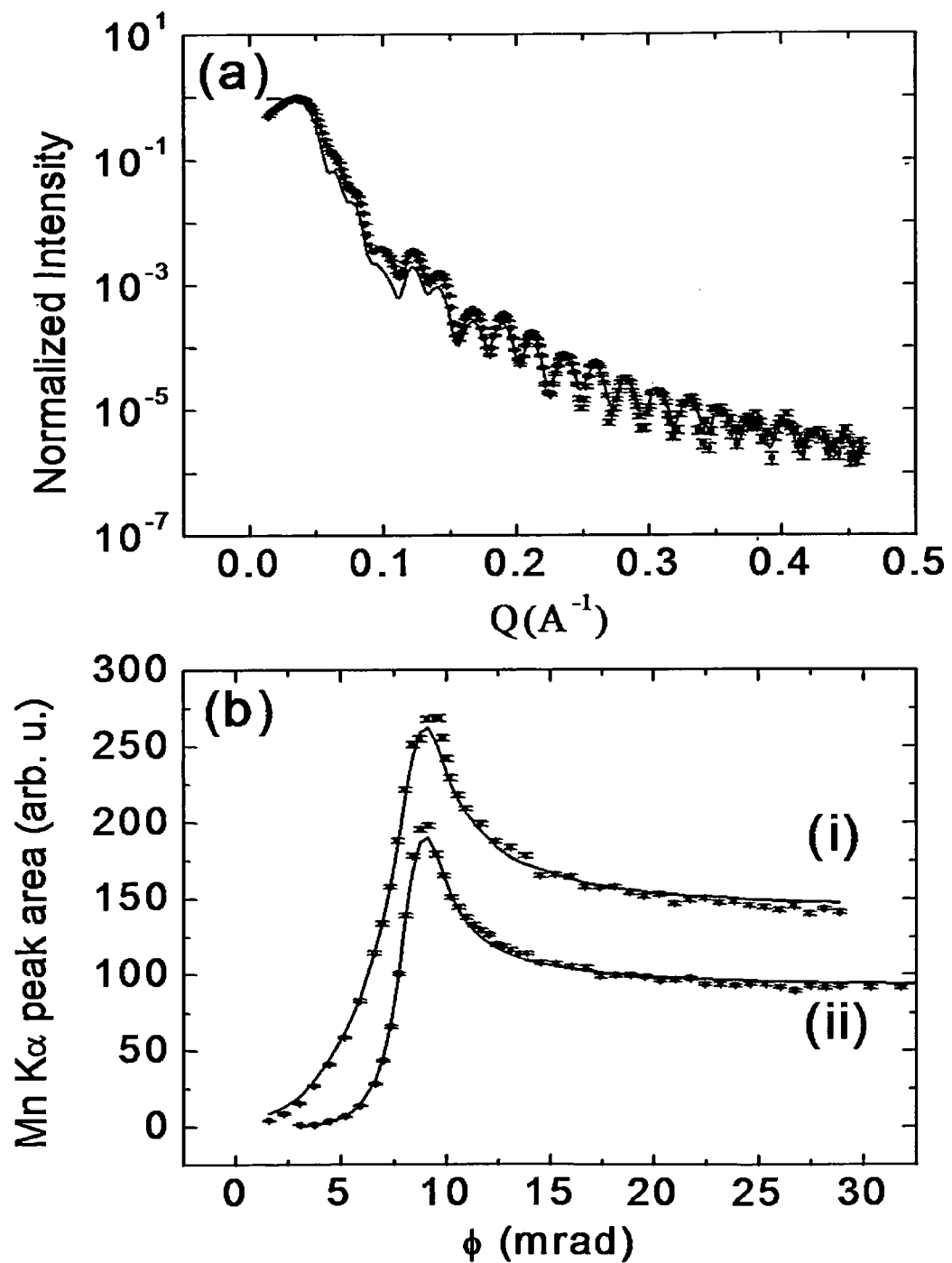
FIG. 4 (a) is an X-ray reflectivity and (b) are RHEED-TRAXS measurements on a Mn film sample. The symbols are the data and the solid curves are the fits to the data. (i) and (ii) correspond to data obtained prior and after the Al deposition, respectively. The parameters used in this fit are shown in Table I.

FIG. 2 shows an example of the x-ray fluorescence obtained from CASINO for a Y (25 nm)/Mn (25 nm)/GaN layered structure. FIG. 3(a) shows the electron trajectories and FIG. 3(b) shows the x-ray depth profile inside Y and Mn layers based the trajectories in FIG. 3(a), with the intensity normalized to the maximum value near the interface. Data such as those shown in FIG. 2(b) were used as the intensity profile in Eq. 6.

For a single layer of Mn on GaN, in-situ estimates of both thickness and roughness matched the ex-situ estimates (Tables I and III). For a single layer of Y on GaN, the thickness estimates were again in good agreement with the ex-situ results, but the roughness estimate differed from the reflectivity result in one case by less than a nanometer (Tables II and IV).

For Al overlayer, the thickness estimates for Al from the Y signal and the Y layer itself were worse than that obtained in case of Al overlayer on Mn. This was partly because of the reduced signal quality of already small Y peak. Also, Al layer on top of Mn or Y caused the x-rays to bend towards the normal to the surface causing the sharpening of the peak at the critical angle. The effect, most prominent around the critical angle, gave Mn, with critical angle at about 9 mrad, more sensitivity to Al overlayer parameters compared to Y with critical angle at about 3 mrad (Eqs. 3 and 5). Hence, Al overlayer thickness determination using Mn yielded better results, in general.

Figure 5:
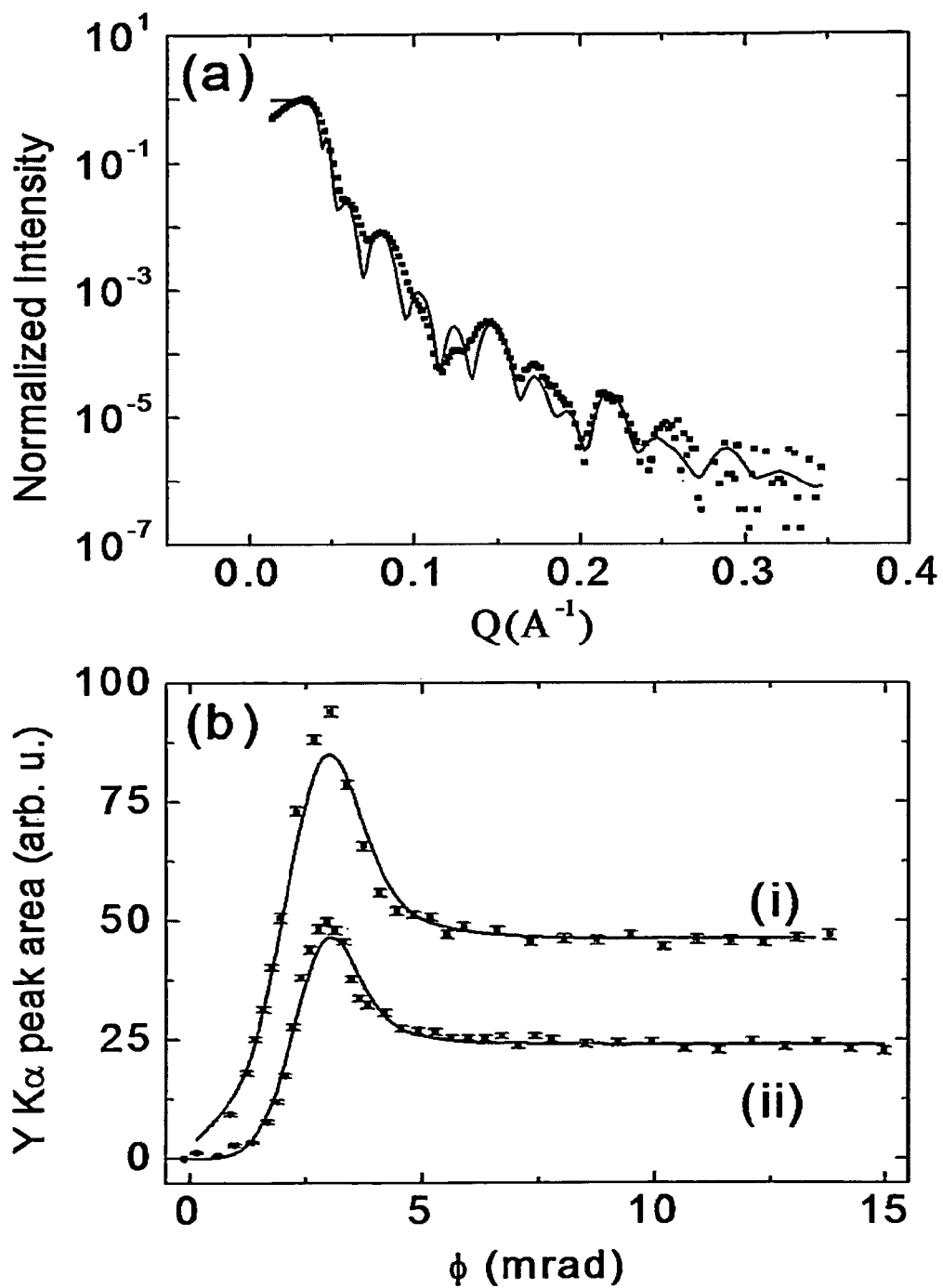
FIG. 5 (a) are X-ray reflectivity and (b) are RHEED-TRAXS measurements on a Y film sample. The symbols are the data and the solid curves are the fits to the data. (i) and (ii) correspond to data obtained prior and after the Al deposition, respectively. The parameters used for the fits are shown in Table II.
Figure 6:
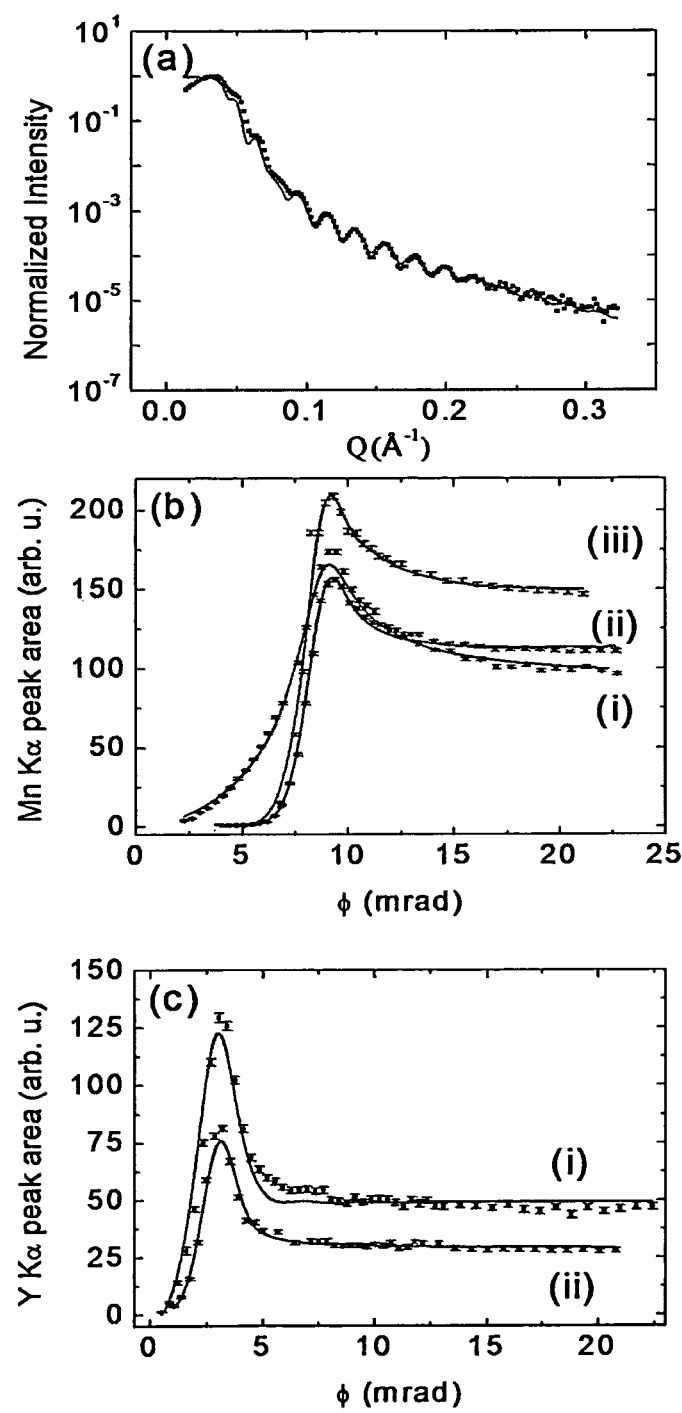
FIG. 6 (a) are X-ray reflectivity and RHEED-TRAXS measurements using (b) are Mn $K\alpha$ fluorescence and (c) are Y $K\alpha$ fluorescence on the GaN/Mn/Y/Al sample. In (b), (i), (ii) and (iii) are data obtained after deposition of the Mn layer, the Y layer and the Al layer, respectively. Symbols represent the data, solid curves fits to the data. In (c), (i) and (ii) are data obtained after the deposition of Y layer and the Al layer. The parameters used for the fits are shown in Table III.
Figure 7:
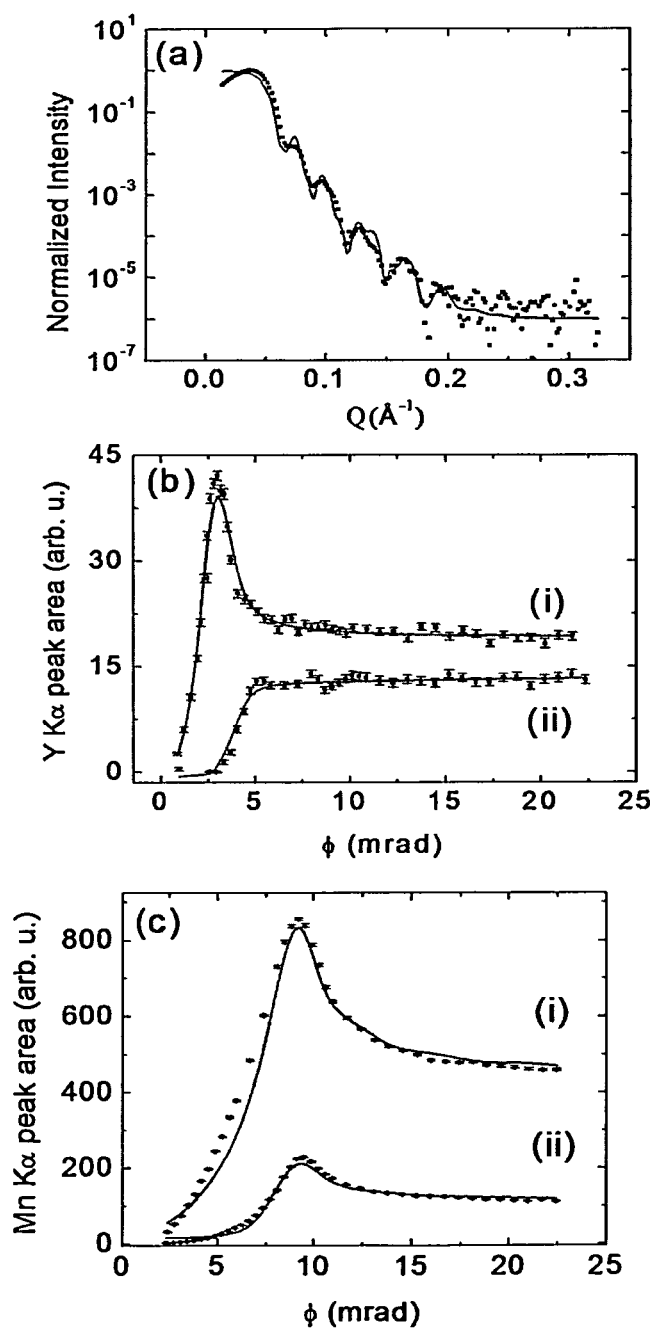
FIG. 7 (a) are X-ray reflectivity and RHEED-TRAXS measurements using (b) is Y $K\alpha$ fluorescence and (c) is Mn $K\alpha$ fluorescence on the GaN/Y/Mn/Al sample. In (b), (i) and (ii) are data obtained after deposition of the Y layer and the Mn layer, respectively. In (c), (i) and (ii) are data obtained after deposition of the Mn layer and the Al layer. Symbols represent the data, solid curves fits to the data. The parameters used for the fits are shown in Table IV.

While investigating the Y/Mn and Mn/Y bilayers (FIGS. 5 and 6), thickness estimates were comparable to ex-situ results for the investigated layer buried under several nanometers of a different material. Mn fluorescence showed sensitivity to the Y underlayer thickness which was worse than that for an overlayer, but Mn underlayer thickness could not be determined using Y fluorescence. The thickness of Mn layer under Y was held fixed during the fitting process (Table III). The lower sensitivity towards the underlayer parameters was because of a much smaller contribution of $E_n^R$ towards the total detected intensity than E. As a variation in the underlayer parameters such as thickness was reflected, to a greater degree, in the variation in $E_n^R$, it was harder to detect by fitting the angular dependence of the total intensity.

For Mn/Y bilayer, Y fluorescence from Y layers buried below Mn and Al was greatly attenuated. Mn, once again, gave reasonable estimates for Mn layer and even showed sensitivity for Y underlayer, unlike the Y signal in Y/Mn bilayer. Another remarkable feature was the angular dependence of Y fluorescence from under the Mn layer that showed no peak at the critical angle. Though the behavior was matched by the theory, the fitting process revealed that the thickness sensitivity for Y layer was poor. Also, once covered with Al and Mn overlayers, the Y signal was too small to be analyzed.

We have demonstrated that the angular dependence of x-ray fluorescence near the critical angle can be analyzed within the kinematic approach to yield useful structural information (i.e., layer thickness and interface roughness) not only about a single thin film but also for a multilayered structure. Hence, it is possible to perform in-situ quantitative structural characterization without the use of any standards.

Moreover, the fluorescence from a buried layer can be used to probe the properties of the overlayer, whose fluorescence may not be easily analyzable because of the detector efficiency curve. Another possible use is to probe surface phenomena such as precipitation and layer formation because the coverage of the investigated layer caused a detectable change in the fluorescence angular dependence.

The use of the reciprocity theorem simplified the theoretical implementation, as compared with direct calculations [16], and allowed us to generalize the model for multilayered structures. The computational requirements were also modest for a single layer as the Monte Carlo simulation was carried out just once. For multilayered samples, the simulation was carried out iteratively using the thickness values from the angular dependence fitting routine, but the convergence was reached in 2 to 3 iterations.

The signal quality data collection times used in our demonstrations were unsuitable for real-time analysis. The most significant issues to be addressed are the weak signal and the reproducibility of the electron beam positioning. Improvement in control of the electron beam positioning should help reduce the artifacts due to beam drift. Suitable modifications to the system design to place the detector close to the sample should increase the count rate and allow the usage of a narrower slit width for better resolution and a faster silicon drift detector (SDD) to handle high count rates. These modifications will enable real-time analysis.

Tables

TABLE I

Structural parameters for the GaN/Mn/Al sample obtained from x-ray reflectivity (XRR) and RHEED-TRAXS. The thickness of the layer is d and the interfacial roughness is σ. The uncertainties in the values were obtained from the non-linear least squares fit procedure. The Mn_GaN data were obtained after the Mn deposition and the Al_Mn_GaN profile was obtained after the Al layer deposition. The characteristic x-ray peak used for the data analysis is indicated.

| | | | Al | | Mn | | GaN |
|---|---|---|---|---|---|---|---|
| Layer Material | | | d (nm) | s (nm) | d (nm) | s (nm) | s (nm) |
| XRR | | | 10 ± 2 | 0.9 ± 0.9 | 26.1 ± 0.5 | 0.2 ± 0.1 | 0.2 ± 0.2 |
| RHEED-TRAXS | | | | | | | |
| Profile | Peak | | | | | | |
| Mn_GaN | Mn Kα | | — | — | 23 ± 3 | 1 ± 1 | — |
| Al_Mn_GaN | Mn Kα | | 8.3 ± 0.4 | — | 25 ± 2 | 1 ± 1 | — |

TABLE II

Structural parameters for the GaN/Y/Al sample obtained from x-ray reflectivity (XRR) and RHEED-TRAXS. The thickness of the layer is d and the interfacial roughness is σ. The uncertainties in the values were obtained from the non-linear least squares fit procedure. The Y_GaN data were obtained after the Y deposition and the Al_Y_GaN profile was obtained after the Al layer deposition. The characteristic x-ray peak used for the data analysis is indicated.

| | | Al | | Y | | GaN |
|---|---|---|---|---|---|---|
| Layer Material | | d (nm) | s (nm) | d (nm) | s (nm) | s (nm) |
| XRR | | 8.6 ± 0.8 | 0.8 ± 0.4 | 18 ± 1 | 0.3 ± 0.4 | 0.7 ± 0.4 |
| RHEED-TRAXS results | | | | | | |
| Profile | Peak | | | | | |
| Y_GaN | Y Kα | — | — | 19 ± 2 | 1.9 ± 0.4 | — |
| Al_Y_GaN | Y Kα | 15 ± 8 | — | 13 ± 7 | 5 ± 2 | — |

TABLE III

Structural parameters for the GaN/Mn/Y/Al sample obtained from x-ray reflectivity (XRR) and RHEED-TRAXS. The thickness of the layer is d and the interfacial roughness is σ. The uncertainties in the values were obtained from the non-linear least squares fit procedure. The Mn_GaN, Y_Mn_GaN, Al_Y_Mn_GaN data were obtained after the Mn, Y, and Al depositions, respectively. The characteristic x-ray peak used for the data analysis is indicated.

| | | Al | | Y | | Mn | | GaN |
|---|---|---|---|---|---|---|---|---|
| Layer Material | | d (nm) | s (nm) | d (nm) | s (nm) | d (nm) | s (nm) | s (nm) |
| XRR | | 12 ± 3 | 2 ± 1 | 12 ± 5 | 3 ± 2 | 28 ± 2 | 0.2 ± 0.9 | 0.8 ± 0.2 |
| RHEED-TRAXS | | | | | | | | |
| Profile | Peak | | | | | | | |
| Mn_GaN | Mn Kα | — | — | — | — | 29 ± 4 | 1 ± 2 | — |
| Y_Mn_GaN | Y Kα | — | — | 15 ± 1 | 3 ± 0.4 | 28[a] | — | — |
| Y_Mn_GaN | Mn Kα | — | — | 14.6 ± 0.4 | 1.3 ± 0.3 | 28 ± 2 | 0 ± 3 | — |
| Al_Y_Mn_GaN | Y Kα | 9 ± 2 | — | 8.4 ± 0.9 | — | 28[a] | — | — |
| Al_Y_Mn_GaN | Mn Kα | 15 ± 4 | — | 14 ± 2 | — | 29 ± 5 | 1 ± 4 | — |

[a]The parameter was held constant during the fitting process.

TABLE IV

Structural parameters for the GaN/Y/Mn/Al sample obtained from x-ray reflectivity (XRR) and RHEED-TRAXS. The thickness of the layer is d and the interfacial roughness is σ. The uncertainties in the values were obtained from the non-linear least squares fit procedure. The Y_GaN, Mn_Y_GaN, Al_Mn_Y_GaN data were obtained after the Y, Mn, and Al depositions, respectively. The characteristic x-ray peak used for the data analysis is indicated. Y signal from under Al and Mn layers was too week to be analyzed.

| | | Al | | Mn | | Y | | GaN |
|---|---|---|---|---|---|---|---|---|
| Layer Material | | d (nm) | s (nm) | d (nm) | s (nm) | d (nm) | s (nm) | s (nm) |
| XRR | | 9 ± 5 | 1.8 ± 0.9 | 19 ± 1 | 1.4 ± 0.5 | 25 ± 2 | 0.9 ± 0.3 | 1.2 ± 0.9 |
| RHEED-TRAXS | | | | | | | | |
| Profile | Peak | | | | | | | |
| Y_GaN | Y Kα | — | — | — | — | 25 ± 2 | 0 ± 1 | — |
| Mn_Y_GaN | Mn Kα | — | — | 21 ± 2 | 1.2 ± 0.6 | 23 ± 9 | — | — |
| Mn_Y_GaN | Y Kα | — | — | 25 ± 6 | — | 22 ± 21 | — | — |
| Al_Mn_Y_GaN | Mn Kα | 6 ± 1 | — | 16 ± 1 | 0 ± 3 | 27 ± 5 | — | — |

Compositional analysis is another potential application of RHEED-TRAXS that can be of great usefulness for in-situ characterization. If performed real time, it could lead to a better stoichiometry control of the thin film growth process.

In one embodiment, the compositional analysis is measured by detecting changes in the angular dependence due to slight changes in the density of the material resulting from the change in relative compositions of the constituent elements. The changes in density and the molar mass of per unit formula can be linked to the refractive index of the material which in turn, defines the shape of the angular dependence in grazing angle regime. The major advantage of adopting this approach is that there is no need to do absolute measurements that require precise information about the geometry of the setup and good standards for calibration. As demonstrated next, however, the change in the angular dependence due to the change in the refractive index is not large enough to see a change in the angular dependence.

In order to demonstrate the feasibility of this method, a simulation was performed with a perfectly stoichiometric YMnO$_3$ layer on GaN and the theoretical curves for the angular dependences for Y and Mn were produced. Next, slight variations in the concentrations of Y and Mn were analyzed. The variation in composition was accounted for by using the expressions for the dispersion and absorption of the medium respectively, $$\delta = 4.1516 \times 10^{-4} \frac{\rho}{ME^2} \sum_{j=1}^{N} C_j f_{1j} \quad (9)$$

$$\beta = 4.1516 \times 10^{-4} \frac{\rho}{ME^2} \sum_{j=1}^{N} C_j f_{2j} \quad (10)$$

Figure 8:
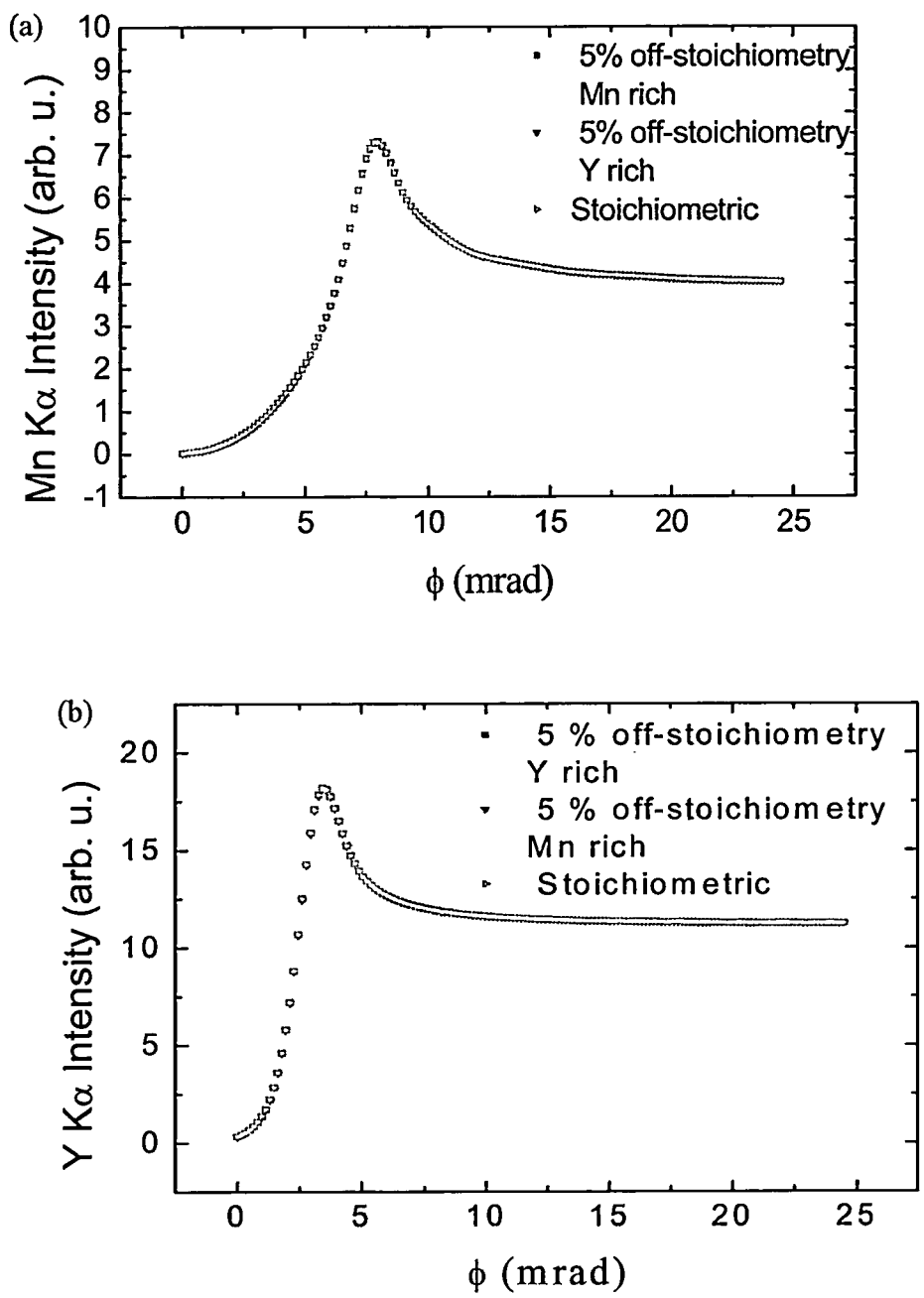
FIG. 8 The variation in the angular dependence of Mn and Y fluorescence coming off 20 nm $YMnO_3$ layer based on the variation in slight change in the refractive index.

Since the mass density (g/cm$^3$) ρ and the molar weight (g/mol) M can be directly linked to compositional coefficients $C_j$ s (number of atoms of type j per molecule) and the atomic scattering factors of atoms of type j $f_j = f_{1j} + f_{2j}$, δ and β can be written as a function of compositional coefficients. Five percent variation in the stoichiometry was analyzed, which corresponded to 2.5 percent variation in the individual compositions of Y and Mn. It was assumed that the fractional compositions add up to a stoichiometric sample such that a Mn deficient sample is Y rich by the same amount. In other words, Mn or Y replaced each other in a non-perfect sample and the amount of oxygen stayed the same. The angular dependence curves are shown in FIG. 8. The curves show little sensitivity to the variation in refractive index. The reason for the insensitivity is apparent from the above equations. The composition sensitive terms ρ,M and the summation terms, are scaled by a very small constant factor, 4.1515×10$^{-4}$. Thus, the variations in the stoichiometry have insignificant effect on δ and β. For 5% Mn rich sample, the change in δ and β is less than 0.1% and about 1%, respectively, for Mn K$_\alpha$ energy. The changes in δ and β for Y K$_\alpha$ energy are also of the same order of magnitude. Thus, the angular dependence was determined to be an insensitive technique for studying stoichiometry. The variation in the refractive index with stoichiometry was ignored in the analysis below based on the current discussion.

In another embodiment, the relative composition of the elements is determined by measuring the relative intensity of the fluorescent signal at any given angle. But the absolute intensity of the signal is also related to the total thickness of the material. Also, because the material has a different refractive index for x-rays of different energy, the absorption effects and rate of increase of the fluorescent signal with increasing thickness is different for each material. Because of the difference in critical angle and overall angular dependence of the signal, the effective measured ratio changes with the take-off angle.

In another embodiment, the relative composition of the elements is determined by measuring the x-ray fluorescence intensity at a fixed take-off angle larger than the critical angle corresponding to the characteristic x-rays corresponding to each of the elements that is measured. For YMnO$_3$, for example, the knowledge of the sample thickness and the relative yields of Mn and Y should help us associate a relative composition to an observed Y to Mn peak ratio. With this idea in mind, two thin Y/Mn bilayer samples were grown on a sapphire (001) substrate. First, an approximately 15 nm thick Mn layer was deposited on sapphire and the RHEED-TRAXS data was collected. Sapphire was used in order to eliminate the secondary fluorescence in Mn due to Ga in the regular GaN substrate. After performing RHEED-TRAXS measurements on the Mn layer, an approximately 15 nm thick layer of Y was deposited and the RHEED-TRAXS measurements were repeated. Y on top could not be fluoresced by Mn under it, so a good estimate of relative intensities due to electron excitation only could be obtained. Depositing Mn and Y on the same substrate ensured that the experimental conditions for both the layers were similar.

Figure 9:
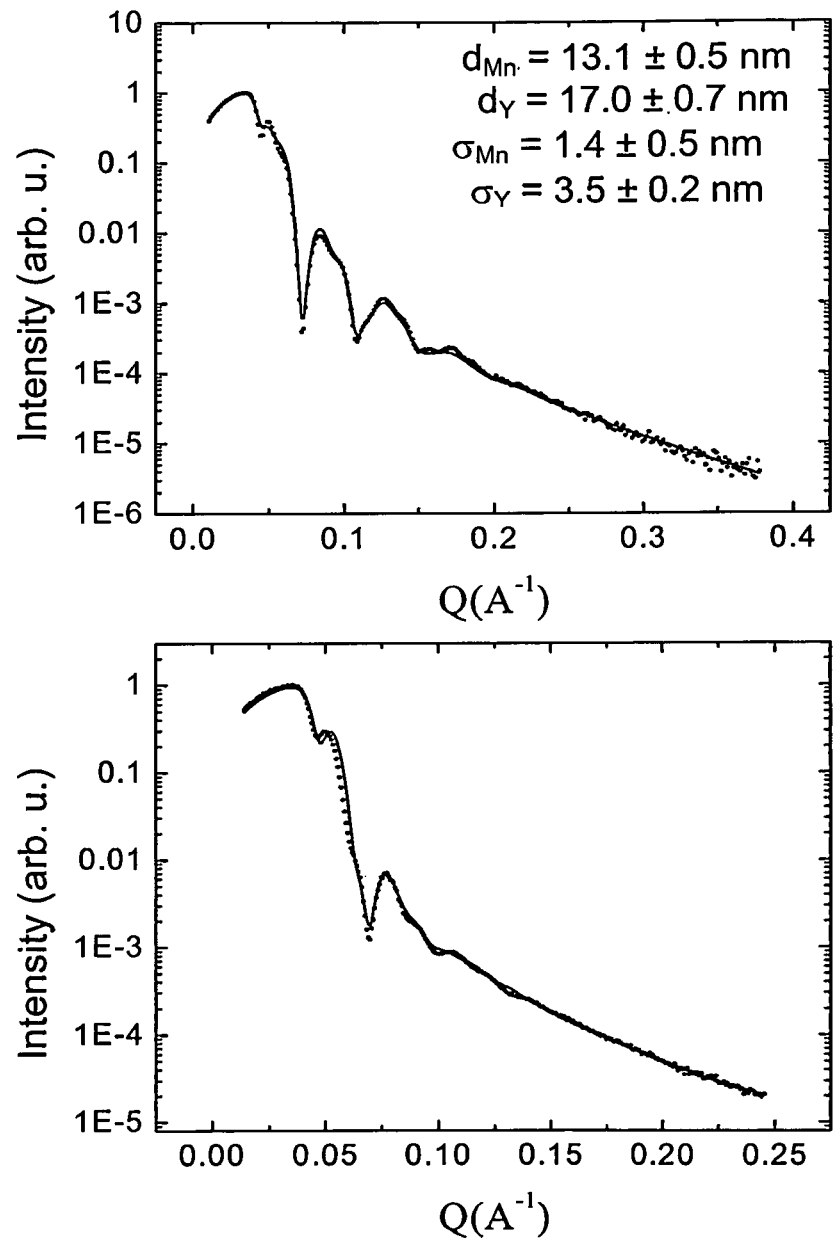
FIG. 9 XRR fitting and thickness estimates for Y/Mn bilayer samples used for estimating relative sensitivity of Mn and Y. Dots are the data and curve is the fit to the data using Parratt's model.

The reproducibility of the conditions from sample to sample was extremely difficult to achieve as slight variations in the sample height and the rotation of the substrate manipulator could affect the count rate outside the error range. Therefore, peak ratio intensity analysis was preferred over the absolute measurements that required reproducibility across samples. Once the samples were removed from the chamber, XRR measurements were performed on them after Al deposition to obtain a more accurate estimate of thickness value than those achievable by RHEED-TRAXS (FIG. 9).

Mn has a much stronger signal than Y for the same experimental conditions and the same thickness of the film. This difference in signal strength is attributable to the difference in fluorescent yield and ionization cross-section of the elements and the difference in detector efficiency. These factors could be combined in a sensitivity factor S, dependent upon the element being investigated. To estimate S, the peak area ratios of Y and Mn at high angles, scaled by appropriate normalization factor based on experimental conditions and thickness values, were used. Normalization was carried out to estimate the relative response of Y and Mn atoms in terms of the peak area. Since it is known that at a high angle the fluorescence intensity is proportional of the thickness of the film for thin films, the following approach was adopted to estimate S.

Suppose the length of the sample illuminated by the electron beam was l, the beam width was w and the thickness of the layer was d. Then the number of atoms of Y or Mn contained in the volume lwd was proportional to $(\rho N_a/A)lwd$, where $\rho$ is the mass density of the material in g/cm$^3$, $N_\alpha$ is the Avogadro's number and A is the atomic mass. The normalized peak area $I^{scaled}(\phi)$ could be related to $I(\phi)$, the experimentally recorded area at an angle $\phi$, for Mn and Y, as follows.

$$I_{Mn}^{scaled}(\phi) = \frac{I_{Mn}(\phi)}{K_{Mn}(\rho_{Mn} N_a / A_{Mn})lwd_{Mn}}, \quad (11)$$

$$I_Y^{scaled}(\phi) = \frac{I_Y(\phi)}{K_Y(\rho_Y N_a / A_Y)lwd_Y}, \quad (12)$$

$$K_{Mn,Y} \propto i_{Mn,Y} t_{Mn,Y}. \quad (13)$$

K depended on the geometry of the setup, acquisition time t and emission current i, $\rho_{Mn}$, $\rho_Y$ are 7.3 and 4.46 g/cm$^3$, respectively, and the thickness of the layers was estimated using XRR.

The sensitivity factor S could be calculated as $$S_{Mn/Y} = \frac{I_{Mn}^{scaled}(\phi)}{I_Y^{scaled}(\phi)} = \frac{I_{Mn}(\phi)}{i_{Mn}t_{Mn}(\rho_{Mn}/A_{Mn})d_{Mn}} \bigg/ \frac{I_Y(\phi)}{i_Y t_Y (\rho_Y / A_Y) d_Y}. \quad (14)$$

Figure 10:
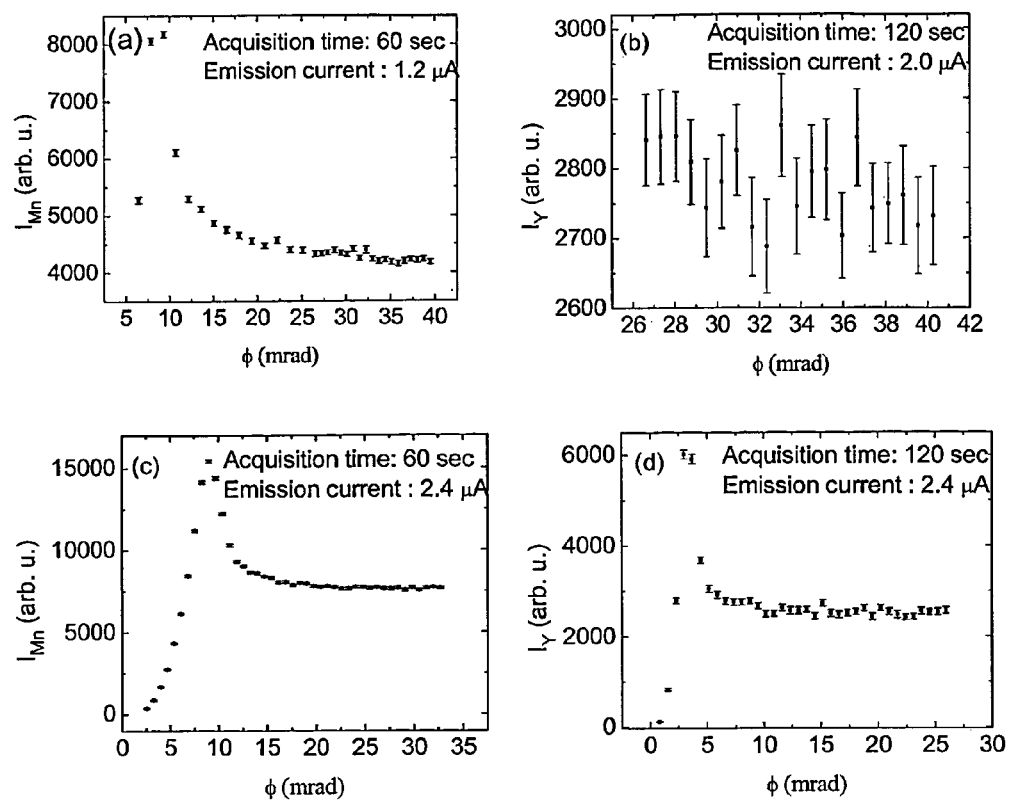
FIG. 10 RHEED-TRAXS angular dependence for two Y/Mn bilayer samples. (a) and (b) are Mn and Y angular dependences for 13.1±0.5 nm thick Mn and 17.0±0.7 nm thick Y in first bilayer sample. Peak areas at angles greater than 26 mrad were used to calculate the ratio in Equation 50. (c) and (d) are Mn and Y angular dependences for 15.1±0.5 nm thick Mn and 18.7±0.6 nm thick Y in the second bilayer sample. Peak areas greater at angles greater than 21 mrad were used to calculate the ratio in Equation 14.

FIG. 10 shows the recorded Mn and Y peak areas for two Y/Mn bilayer samples. Using the peak areas at high angles $\phi > 26$ mrad for (a) and (b) and 26 mrad for (c) and (d)] for the samples, the sensitivity factor was calculated as $$S_{Mn/Y} = 2.71 \pm 0.08 \quad (15)$$

from the two samples analyzed.

Since the signal is independent of angle at high angles, scans at various high angles are equivalent to performing multiple scans at one of those positions. Assuming that the peak areas at various angles represent the samples from the same population, the standard error in the mean of peak area ratios was scaled by scaled by $1/\sqrt{n}$ to obtain the error estimate reported in Eq. 15.

This sensitivity factor obtained could be used to scale the relative intensities of Y and Mn in YMnO$_3$ sample and estimate their relative composition. Since the factor was reached without considering the effects of secondary fluorescence, the ratio obtained from YMnO$_3$ sample should show some enhancement in the Mn signal and reduction in Y signal as some part of the Y fluorescence would excite Mn atoms.

To test this approach on a compound material, RHEED-TRAXS measurements were performed on three YMnO$_3$ samples of different thickness values and the results compared with Rutherford Backscattering (RBS) and x-ray photoelectron spectroscopy (XPS) measurements. RHEED-TRAXS measurements were taken after removing the samples from the chamber and mounting them on a clean alumina block. The peak ratios were also calculated at various angles and compared with theoretical predictions after being scaled by the sensitivity factor described in the previous section. Comparing the results with RBS measurements yielded important information that could be used to study relative composition real time and possibly control the stoichiometry. XRR measurements were also performed to get a better estimate of the sample thickness values (FIG. 11).

Figure 12:
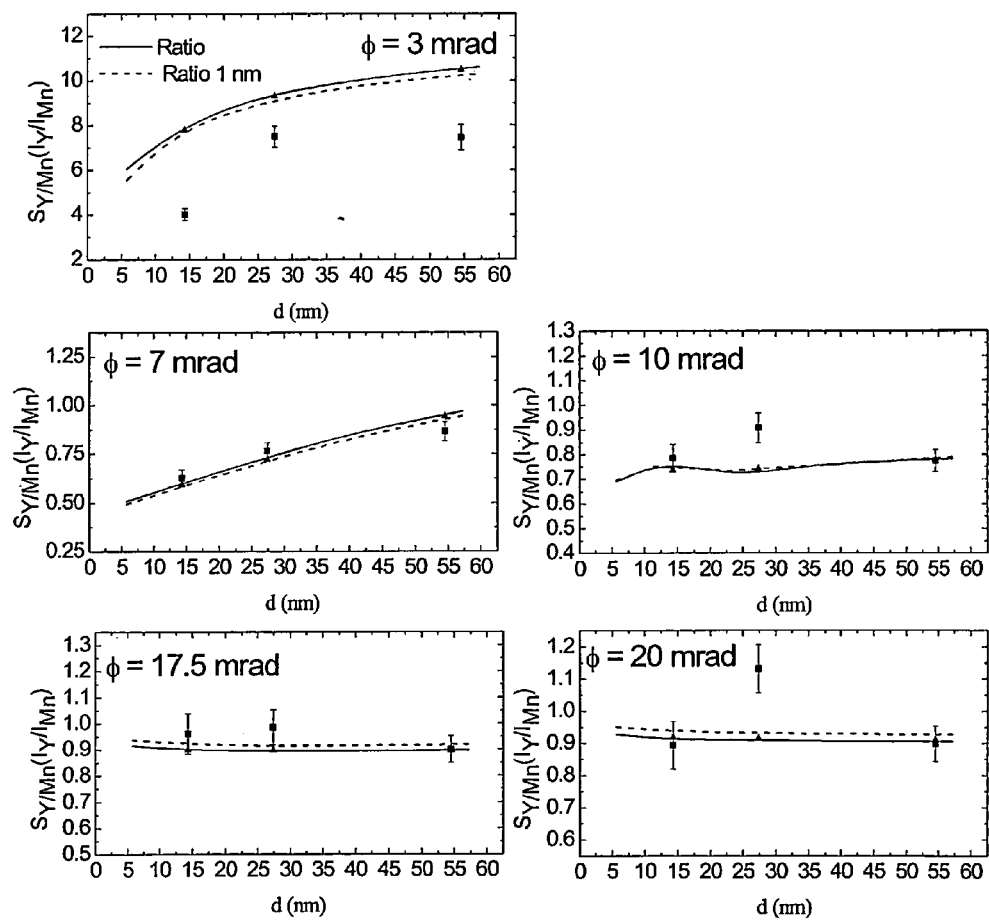
FIG. 12 Theoretical curves and experimental data for the thickness dependence of Y to Mn $K_\alpha$ peak ratios at various angles in $YMnO_3$ samples. The data points are reached upon by scaling the experimental peak ratios by the sensitivity factor as described in Equation 16. The solid curves are for smooth samples, dashed curves are for a roughness of 1 nm and triangles are the simulation results using the real roughness values for the samples as determined using XRR measurements shown in FIG. 10 (a)-(c).

FIG. 12 shows the theoretical curves for Y to Mn peak area ratios after considering the relative sensitivity for both elements, in the perfectly stoichiometric sample, and the experimental values obtained from three samples after being scaled by the sensitivity factor. The experimental data points in FIG. 12 were derived from Y and Mn peak areas using $$\text{Ratio} = \frac{I_Y(\phi)}{I_{Mn}(\phi)} \bigg|_{Scaled} = S_{Mn/Y} \frac{I_Y(\phi)}{I_{Mn}(\phi)} = (2.71 \pm 0.08) \frac{I_Y(\phi)}{I_{Mn}(\phi)}. \quad (16)$$

Figure 11:
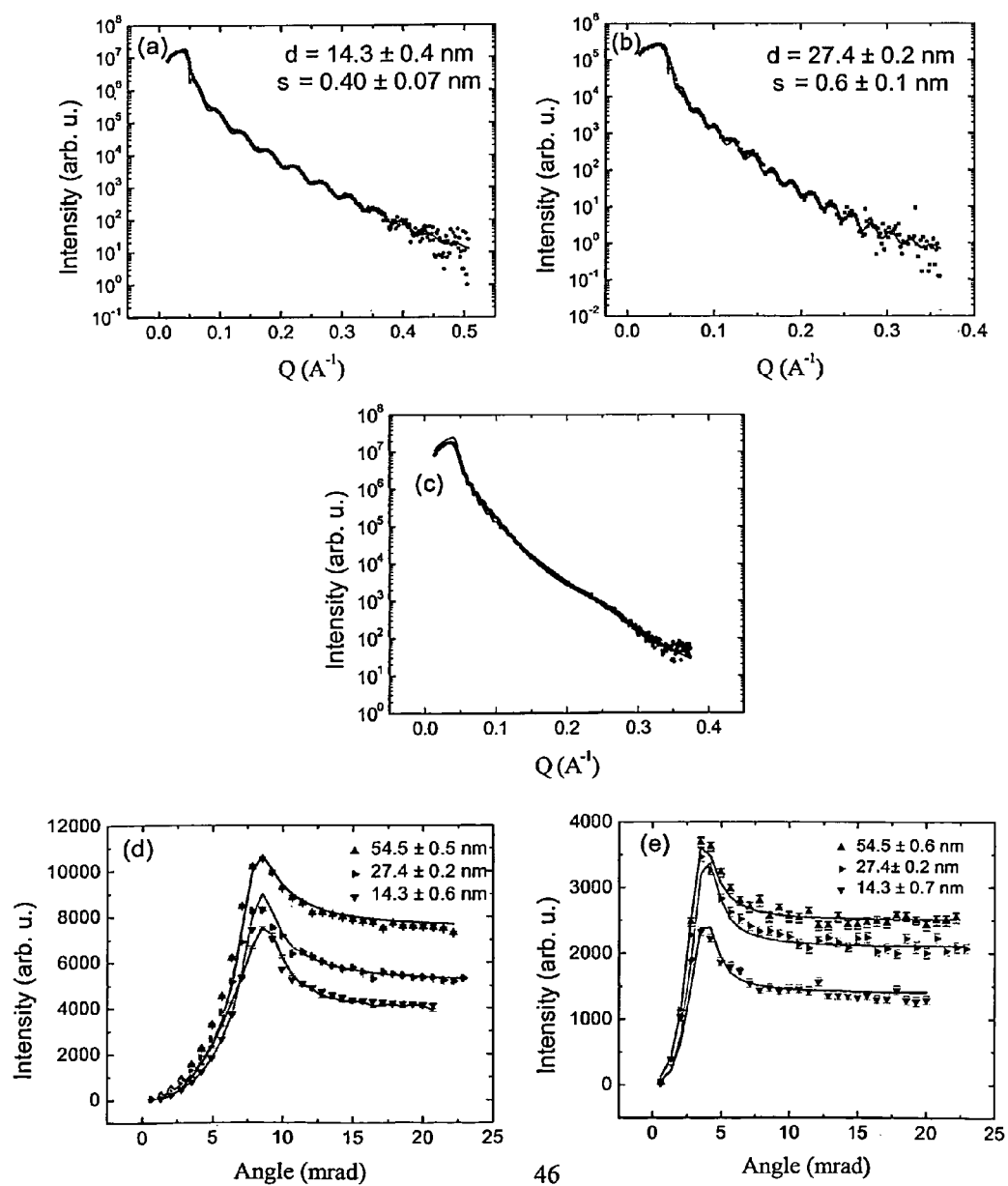
FIG. 11 (a-c) XRR scans and best fits with layer thickness d and roughness σ, (d-e) RHEED-TRAXS scans and simulation based on the thickness values obtained by XRR for the 3 samples analyzed using RBS and XPS measurements. The layer thickness values are shown in the legend.

The calculation for S is discussed in [0057] above and $I_Y(\phi)$, $U_{Mn}(\phi)$ are taken from the angular dependences shown in FIG. 11. Thickness values used in FIG. 12 are from XRR estimates shown is FIG. 11. The experimental values match the theoretical curves at high angles, but at 3 mrad, which is the critical angle for Y, all the values are below the theoretical predictions. This is best understood by considering the secondary fluorescence effect and realizing, after RBS measurements, that all the samples are slightly Y rich. The sensitivity factor used to scale the experimental data points did not consider the attenuation of Y signal and the enhancement of Mn signal due to secondary fluorescence. Hence, it underestimated the Y/Mn ratio from YMnO$_3$. At a take-off angle of $\phi = 3$ mrad, only a small region close to the surface was being probed, so the reduction in Y signal due to Mn excitation was significant. As more material is probed by moving to a higher angle, the excess Y in the film compensated for the secondary effects and moved the data points closer to the theoretical curves. In a perfectly stoichiometric sample, the experimental data points should be below the theoretical curves at all angles, as long as the same sensitivity factor is used. Nonetheless, the most important result was that at a high angle, where the critical angle peak for both materials has flattened out, the relative composition could be studied independently of the sample thickness by analyzing the peak ratio. This was an important result because it suggested a possibility of real time analysis.

Figure 13:
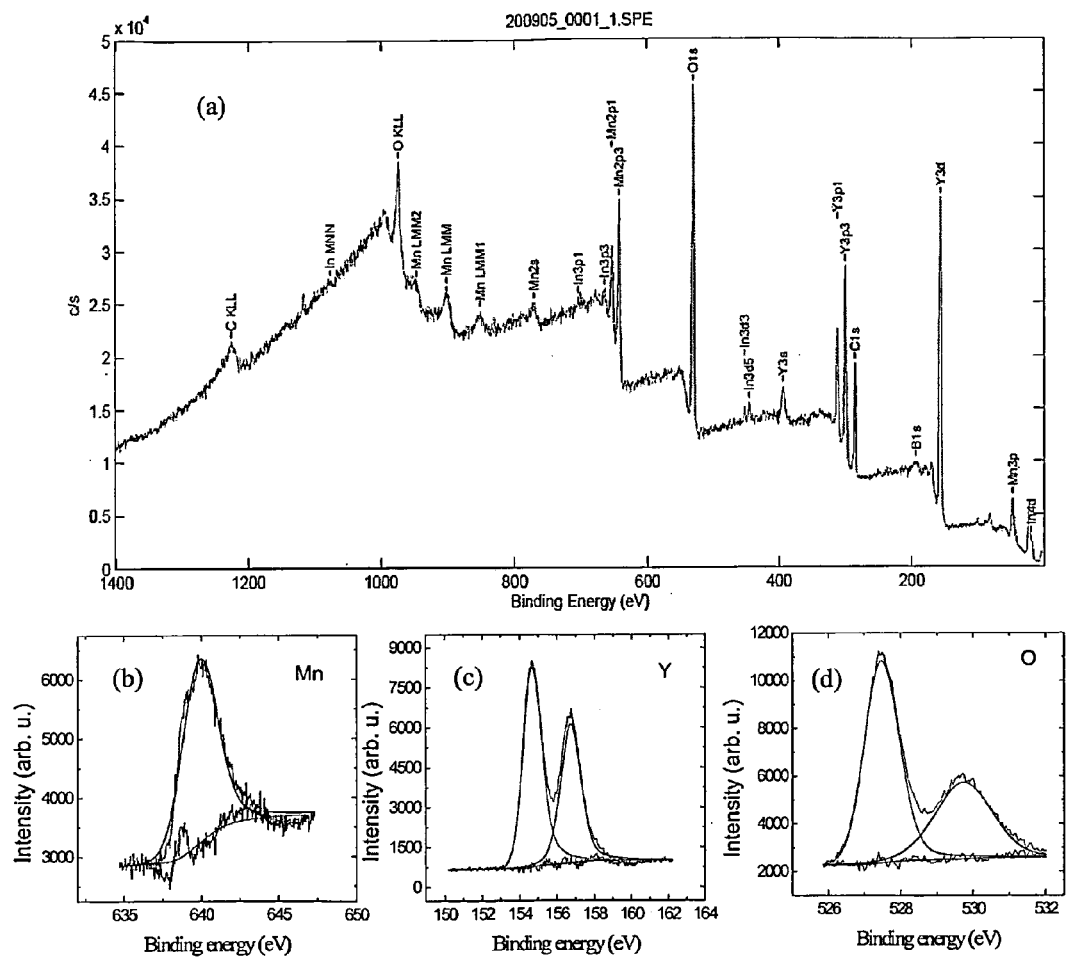
FIG. 13 The XPS survey scan (a) and the detailed scans (b-d) of 54.5 nm thick $YMnO_3$ sample used to determine the relative compositions of Y, Mn and O. The survey scan shows both photoelectric electrons and Auger electrons peaks. The peaks labeled as KLL, MNN and LMM are the Auger peaks.

XPS results for the 54.5 nm thick sample are shown in FIG. 13. FIG. 13 (a) shows the wide survey scan to capture the whole spectrum. The scans were then narrowed down to the peaks of interest; Y, Mn and O, in our case. The carbon peak was due to sample surface contamination due to handling. FIG. 13 (b-d) shows the refined scan to better estimate the percent composition of the elements. The survey scan also revealed that there was a significant amount of boron contamination, possibly from the boron nitride crucible used in the Mn k-cell. After that, XPS measurements were also performed on a single layer of Mn to check for the presence of boron, but it showed no boron peak. This suggests that the boron incorporation in $YMnO_3$ was, most possibly, related to the oxygen overpressure during growth.

The relative compositions were deduced from XPS by scaling Y and Mn peak areas by the sensitivity factor found in a standard handbook. The sensitivity factor was based on the pure element standards and yielded a compositional ratio far off from the stoichiometry. According to XPS, the samples have almost twice as much Y as Mn. The ratios are summarized in Table V. Since the RBS results, which do not require any standards for calibration, yielded a ratio quite close to the stoichiometry, the only important feature of XPS results is the consistency in the trend, suggesting that all samples are close to the same stoichiometry point.

Figure 14:
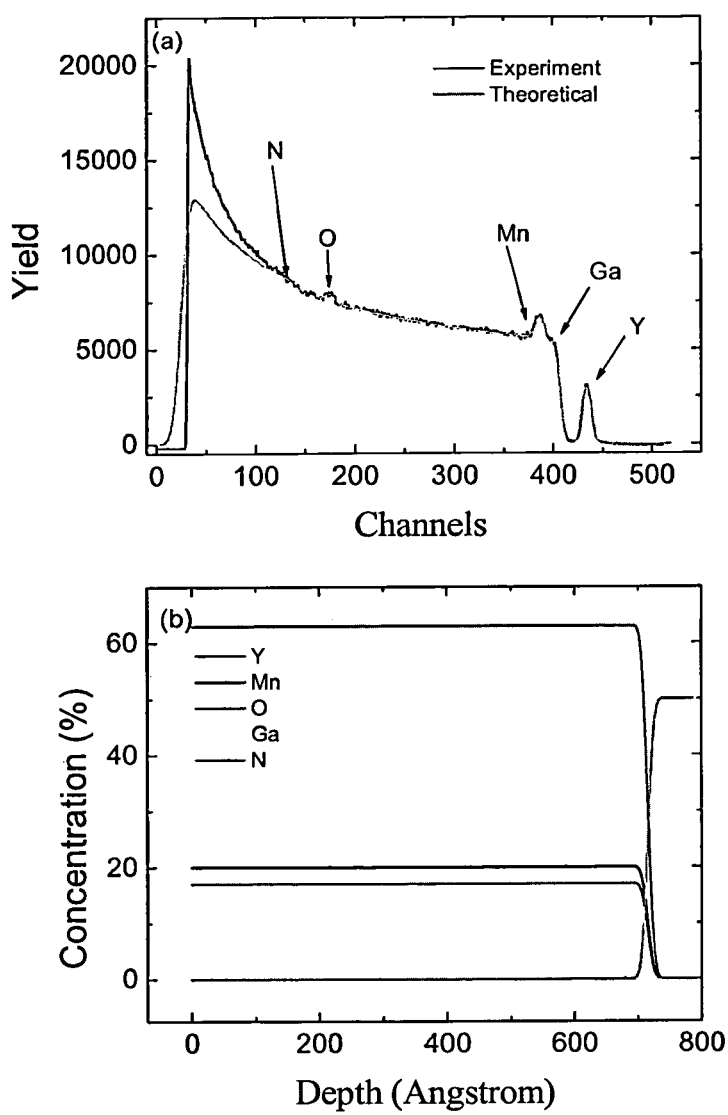
FIG. 14 RBS results for 54.5 nm thick $YMnO_3$ sample. (a) The yield of backscattered He++ ions of 2.275 MeV energy. The detector angle is 108°. The scaled intensities of various peaks give their relative compositions. (b) The relative compositions of Y, Mn, O, Ga and N with depth. The given uncertainty iri the estimates of Y, Mn and O compositions is ±0.5%, ±1%, and ±3% respectively.

RBS has the capability of quantitative compositional analysis without the use of standards and yields information independent of the sensitivity factor for the element (as in XPS and RHEED-TRAXS). The results from RBS for one of the samples are shown in FIG. 14. The results from RBS are also summarized in Table V along with RHEED-TRAXS results. The relative comparison shows that XPS does not have enough sensitivity to distinguish the differences in composition that are resolvable by both RBS and RHEED-TRAXS.

Table V. Comparative table for relative composition of $YMnO_3$ samples. XPS results are off by a constant factor because of the sensitivity factor used and showed lower sensitivity than RBS and RHEED-TRAXS results. RHEED-TRAXS ratios are derived from the average of Y to Mn peak ratios at angles greater than 16 mrad, scaled by the sensitivity factor of 2.71±0.08 for Mn to Y response derived in section 5.2 and correction factor of 1.1 for Mn to Y, to account for the difference in refractive index as shown in FIG. 12.

| Thickness (nm) | Y/Mn compositional ratio | | |
|---|---|---|---|
| | XPS | RBS | RHEED-TRAXS |
| 14.3 ± 0.6 | 2.1 ± 0.4 | 1.08 ± 0.08 | 0.96 ± 0.05 |
| 27.4 ± 0.2 | 2.4 ± 0.5 | 1.3 + 0.1 | 1.16 ± 0.05 |
| 54.5 ± 0.6 | 2.4 ± 0.5 | 1.17 ± 0.09 | 0.98 ± 0.04 |

Figure 15:
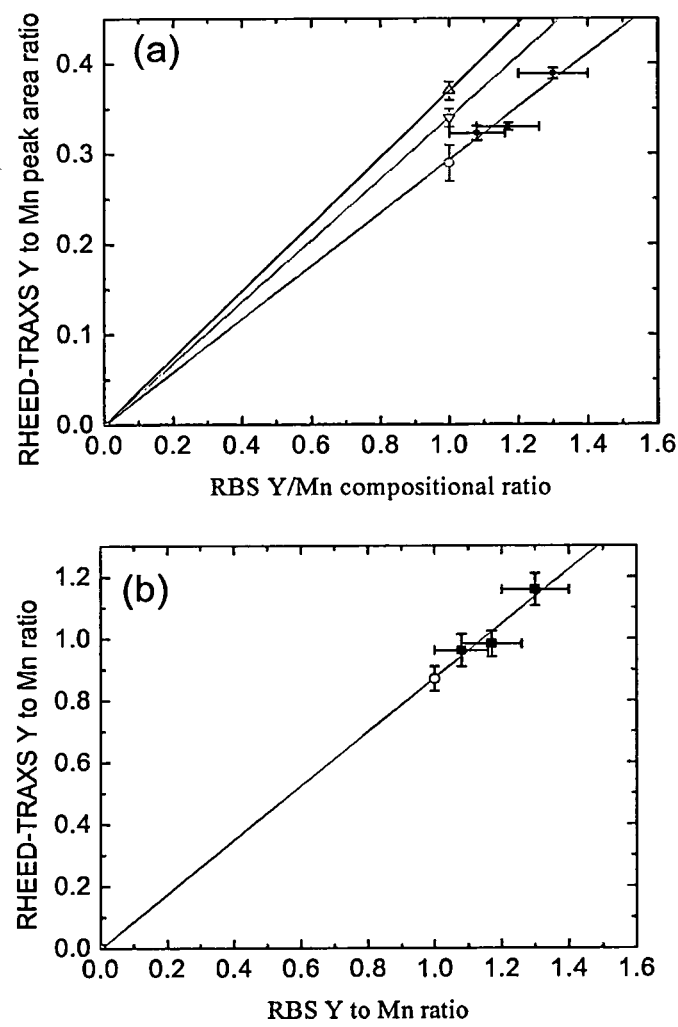
FIG. 15 (a) Average of unsealed Y/Mn peak area ratios at angles greater than 16 mrad for 3 samples. The solid lines are the linear fits. Open triangle at (1, 0.37) is based on relative sensitivity from bilayer samples, inverted triangle at (1, 0.34) is the relative sensitivity factor corrected for refractive indices for Mn and Y energies. Open circle is the stoichiometric point (1, 0.29±0.02) based on the linear fit to data point. (b) A linear fit to the RHEED-TRAXS and RBS results as shown in Table 5. The open circle at (1, 0.87±0.04), based on the linear fit, shows that RHEED-TRAXS underestimated the compositional ratio because of the ignored secondary effects.

In FIG. 15 (a), the ratio of Y to Mn peak areas is an average over 7 to 10 data points at high angles (>16 mrad) and has an uncertainty of about 1%. So the total acquisition time for the reported uncertainties was of the order of 25 minutes, which is unsuitable for real time measurements. For a single two minute scan, the uncertainty is about 6% of the value. FIG. 15 (b) shows a larger uncertainty because of the uncertainty in the scaling factor used.

In FIG. 15 (a) the extrapolated value for a perfectly stoichiometric sample came out to be 0.29±0.02 (for RHEED-TRAXS ratio) and is shown by an open circle. The other two straight lines and triangles correspond to what the ratio should be as predicted by the relative sensitivity of $S_{Mn/Y}=2.71\pm0.08$ or $S_{Y/Mn}=0.37\pm0.01$ (see Eq. 16) and that relative sensitivity $S_{Y/Mn}$ corrected for the difference in the refractive index of $YMnO_3$ for Y and Mn energies. From FIG. 12, Y x-rays are absorbed more than Mn x-rays, yielding a Y/Mn ratio to smaller than one (0.91). Making that correction leads to the value of 0.34±0.01 which is still higher than the 0.29±0.02 as predicted by the linear fit to the data point. The difference between 0.29 and 0.34 is explainable by secondary fluorescence effects. Since, the relative sensitivity and refractive index corrections ignored the fluorescence of Mn by Y radiation, accounting for those effects would diminish the Y signal and increase Mn signal, so the ratio should decrease as suggested by the linear fit. FIG. 15 (b) shows RHEED-TRAXS and RBS relationship after making relative sensitivity and refractive index corrections and it is clear from the graph and RHEED-TRAXS underestimated the Y concentration in all the cases.

The most easily exploitable part of the analysis for real-time analysis is the RHEED-TRAXS peak ratio trend with RBS results. This suggests that while growing the samples, the detector angle could be set at a high angle and Mn and Y compositions can be adjusted according to the change in Y/Mn peak ratios. The results have shown that all the samples grown were Y rich suggesting that the possible desorption of Mn while growing was a key factor in producing a stoichiometric sample. The work is currently underway to systematically study the effect of various factors such as shutter times, substrate temperature and plasma flow on the real time peak ratio measurements with the aim of producing stoichiometric samples.

An embodiment can be a method to determine quantitative structural parameters of a thin film sample wherein the structural parameters are comprised of layer thickness and interfacial roughness. The sample may be composed of a single thin film layer of one material or of multiple thin layers of different materials. The method may be performed by measuring x-ray fluorescence of the sample generated by irradiating the sample with an electron beam at grazing angle incidence as a function of the take-off angle which is the angle outgoing x-rays make with respect to the sample surface. The method can be performed by the of measuring the intensity of x-rays for each characteristic energy corresponding to each chemical element present in the sample as a function of the take-off angle, and then analyzing these data using a model that takes into account the electron beam's penetration, the electron beam's efficiency for x-ray fluorescence within the sample, and then using the optical reciprocity theorem to make a non-linear least-squares fit to the data. This fit yields quantitative values for interface roughness and layer thickness parameters.

Another embodiment may be a method to determine the stoichiometry or the chemical composition of a thin film sample. The sample may be composed of a single thin film layer of one material or of multiple thin layers of different materials. The embodiment may be performed by measuring the intensity of characteristic x-ray fluorescence of each element present in the sample generated by irradiating the sample with an electron beam at grazing angle incidence. X-ray fluorescence or emission can be measured at a take-off angle which is the angle outgoing x-rays make with respect to the sample surface. The take-off angle may be large compared to the critical angle of characteristic x-rays emitted by the element with the largest critical angle. The critical angle is the angle of total external reflection for the characteristic x-ray wavelength. The relative intensities of each element are corrected by sensitivity factors dependent on the electron emission current, time of acquisition, the atomic mass, the material's density, and the thickness of the sample. Relative stoichiometries are determined by dividing scaled intensities for each element by each other. To obtain high precision measurements, calibration may be made by other methods, such as, but not limited to, Rutherford back scattering spectroscopy or any other calibration method known by one skilled in the art. Calibration involves measuring a sample using the procedure and using the alternative method for a known sample, thus obtaining a correction factor that can be used for other unknown samples. The method of can further be performed in-situ and during the fabrication of a film. Methods of thin film fabrication can include, but are not limited to, molecular beam epitaxy, physical vapor deposition, pulsed laser deposition, and sputtering thin film growth. Therefore, the method of in situ performance can be used to provide feedback for growth parameters to optimize stoichiometry during the growth of the film.

Another embodiment may be a determining the structural parameters and the stoichiometry of a thin film sample simultaneously consisting of calculating the measurements of characteristic x-ray fluorescence as a function of take-off angle to angles larger than the critical angle of the element with the largest critical angle, which allows simultaneous determination of structural parameters and stoichiometry.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

REFERENCE LIST

[1] W. Braun, Applied RHEED (Springer, Berlin, 1999).
[2] S. Hasegawa, H. Daimon, and S. Ino, Surface Science 186, 138 (1987).
[3] W. Braun and K. H. Ploog, Journal of Crystal Growth 251, 68 (2003).
[4] T. W. Barbee Jr. and W. K. Warburton, Mater. Lett. 3, 17 (1984).
[5] M. Born and E. Wolf, *Principles of optics* (Cambridge University Press, Cambridge 1999).
[6] R. S. Becker, J. A. Golovchenko, and J. R. Patel, Phys. Rev. Lett. 50, 153 (1983).
[7] G. H. Vineyard, Phys. Rev. B 26, 4146 (1982).
[8] L. G. Parratt, Phys. Rev. 95, 359 (1954).
[9] L. Nevot and P. Croce, Rev. Phys. Appl. 15, 761 (1980).
[10] D. Drouin, et. al. Scanning 29, 92 (2007).
[11] *Origin* (Version 7.5), ©1991-2006, OriginLab Corporation.
[12] *Paratt*32 (Version 1.6.0), ©1997-99, Christian Braun, HMI Berlin.
[13] www.amptek.com (2007).
[14] R. Klockenkamper, *Total reflection X-ray Fluorescence Analysis* (Wiley-Interscience, 1996).
[15] S. Krassimir, K. Sakurai, The Rigaku Journal 14, 22 (1997).
[16] H. P. Urbach and P. K. de Bokx, Phys. Rev. B 53, 3752 (1996).

What is claimed is:

1. A method comprising determining quantitative structural parameters of a thin film sample wherein the quantitative structural parameters are comprised of layer thickness and interfacial roughness wherein the determination comprises
measuring x-ray fluorescence of the sample generated by irradiating the sample with an electron beam at grazing angle incidence as a function of the take-off angle;
measuring the intensity of x-rays for each characteristic energy corresponding to each chemical element present in the sample as a function of the take-off angle; and
analyzing these data to determine the electron beam's penetration, the electron beam's efficiency for x-ray fluorescence within the sample, and using the optical reciprocity theorem to make a non-linear least-squares fit to the data.

2. The method of claim 1 wherein a thin film sample is comprised of a single thin film layer of one material.

3. The method of claim 1 wherein a thin film sample is comprised of multiple thin layers of different materials.

4. The method of claim 1 wherein a thin film sample is comprised of multiple thin layers of one material.

5. The method of claim 1 further comprising simultaneously determining the stoichiometry of a thin film sample wherein the determination comprises
measuring the intensity of characteristic x-ray fluorescence of each element present in the sample generated by irradiating the sample with an electron beam at grazing angle incidence wherein the x-ray fluorescence is measured at a take-off angle wherein the take-off angle is large compared to the critical angle of characteristic x-rays emitted by the element with the largest critical angle and the critical angle is the angle of total external reflection for the characteristic x-ray wavelength;
correcting the relative intensities of each element by sensitivity factors dependent on the electron emission current, time of acquisition, the atomic mass, the material's density, and the thickness of the sample;
determining relative stoichiometries by dividing scaled intensities for each element by each other.

6. The method of claim 5 further comprising calibrating the determined relative stoichiometries by using an alternative method for a known sample and comparing the results to the determined relative stoichiometries to obtain a correction factor that can be used for unknown samples.

7. A method comprising determining the stoichiometry of a thin film sample wherein the determination comprises
measuring the intensity of characteristic x-ray fluorescence of each element present in the sample generated by irradiating the sample with an electron beam at grazing angle incidence wherein the x-ray fluorescence is measured at a take-off angle wherein the take-off angle is large compared to the critical angle of characteristic x-rays emitted by the element with the largest critical angle and the critical angle is the angle of total external reflection for the characteristic x-ray wavelength;
correcting the relative intensities of each element by sensitivity factors dependent on the electron emission current, time of acquisition, the atomic mass, the material's density, and the thickness of the sample;
determining relative stoichiometries by dividing scaled intensities for each element by each other.

8. The method of claim 7 further comprising calibrating the determined relative stoichiometries by using an alternative method for a known sample and comparing the results to the determined relative stoichiometries to obtain a correction factor that can be used for unknown samples.

9. The method of claim 8 wherein the calibration method is Rutherford backscattering spectroscopy.

10. The method of claim 8 further comprising simultaneously determining quantitative structural parameters of a thin film sample wherein the quantitative structural parameters are comprised of layer thickness and interfacial roughness wherein the determination comprises measuring x-ray fluorescence of the sample generated by irradiating the sample with an electron beam at grazing angle incidence as a function of the take-off angle;

measuring the intensity of x-rays for each characteristic energy corresponding to each chemical element present in the sample as a function of the take-off angle; and analyzing these data to determine the electron beam's penetration, the electron beam's efficiency for x-ray fluorescence within the sample, and using the optical reciprocity theorem to make a non-linear least-squares fit to the data.

11. The method of claim 7 wherein a thin film sample is comprised of a single thin film layer of one material.

12. The method of claim 7 wherein a thin film sample is comprised of multiple thin layers of different materials.

13. The method of claim 7 wherein a thin film sample is comprised of multiple thin layers of one material.

14. The method of claim 7 wherein the structural parameters and stoichiometry of the film can be performed in-situ and during the fabrication of a film wherein the methods of thin film fabrication consist of molecular beam epitaxy, physical vapor deposition, pulsed laser deposition, and sputtering thin film growth.

15. The method of claim 14 wherein the in situ performance provides feedback for growth parameters to optimize stoichiometry during the growth of the film.

16. The method of claim 7 further comprising simultaneously determining quantitative structural parameters of a thin film sample wherein the quantitative structural parameters are comprised of layer thickness and interfacial roughness wherein the determination comprises measuring x-ray fluorescence of the sample generated by irradiating the sample with an electron beam at grazing angle incidence as a function of the take-off angle;

measuring the intensity of x-rays for each characteristic energy corresponding to each chemical element present in the sample as a function of the take-off angle; and analyzing these data to determine the electron beam's penetration, the electron beam's efficiency for x-ray fluorescence within the sample, and using the optical reciprocity theorem to make a non-linear least-squares fit to the data.

* * * * *